United States Patent
Wu et al.

(10) Patent No.: US 11,959,066 B2
(45) Date of Patent: Apr. 16, 2024

(54) PSEUDOMONAS MONTEILII STRAIN AND APPLICATION THEREOF IN THE DEGRADATION OF PETROLEUM HYDROCARBONS IN SALINE-ALKALI ENVIRONMENT

(71) Applicant: Northwest Institute of Eco-Environment and Resources, CAS, Lanzhou (CN)

(72) Inventors: Yingqin Wu, Lanzhou (CN); Zhiyu Wang, Lanzhou (CN); Tong Wang, Beijing (CN); Longmiao Yuan, Lanzhou (CN); Yanhong Liu, Lanzhou (CN); Rong Ma, Lanzhou (CN)

(73) Assignee: Northwest Institute of Eco-Environment and Resources, CAS, Lanzhou (CN)

( * ) Notice: Subject to any disclaimer, the term of this patent is extended or adjusted under 35 U.S.C. 154(b) by 0 days.

(21) Appl. No.: 18/149,950

(22) Filed: Jan. 4, 2023

(65) Prior Publication Data
US 2023/0365917 A1 Nov. 16, 2023

(30) Foreign Application Priority Data
Jan. 5, 2022 (CN) .......................... 202210006424.3

(51) Int. Cl.
*C12N 1/20* (2006.01)
*B09C 1/10* (2006.01)

(52) U.S. Cl.
CPC . *C12N 1/20* (2013.01); *B09C 1/10* (2013.01)

(58) Field of Classification Search
CPC ............. C12N 1/26; C12N 15/78; C12N 1/20
See application file for complete search history.

(56) References Cited

FOREIGN PATENT DOCUMENTS

| CN | 110499264 A | 11/2019 |
|---|---|---|
| WO | 2006069035 A2 | 6/2006 |

OTHER PUBLICATIONS

Anelise Stella Ballaben et al.,"Extensively drug-resistant IMP-16-producing Pseudomonas monteilii isolated from cerebrospinal fluid", Infection, Genetics and Evolution, 104658.
Qingyuan Li et al., "The Utilization Efficiency of Pseudomonas monteilii to Edible Fats and Oils", Food and Nutrition in China, vol. 25, No. 8, pp. 46-49, abstract translated only.
Jincheng Wang et al., "Impact of Crude Oil Pollution on Soil Biological and Abiological Properties in Eastern Gansu Province", Bulletin of Soil and Water Conservation, Feb. 2017, vol. 37, No. 1, pp. 009-016, abstract translated only.

*Primary Examiner* — Brian Gangle
*Assistant Examiner* — Lakia J Jackson-Tongue

(57) ABSTRACT

A *Pseudomonas monteilii* strain with salinity-alkalinity tolerance is provided. The strain is *Pseudomonas monteilii* 9-2, which has been deposited in China General Microbiological Culture Collection Center (CGMCC) on Oct. 25, 2021, with an accession number of CGMCC No. 23666; and an internal transcribed spacer (ITS) sequence is shown in SEQ ID NO: 1. This application further provides an application of the *Pseudomonas monteilii* strain in the degradation of petroleum hydrocarbons in a saline-alkali environment.

6 Claims, 6 Drawing Sheets

Specification includes a Sequence Listing.

SEQUENCE LISTING

```
Sequence total quantity: 1
SEQ ID NO: 1           moltype = DNA  length = 1125
FEATURE                Location/Qualifiers
source                 1..1125
                       mol_type = other DNA
                       note = Artificial sequence
                       organism = synthetic construct
SEQUENCE: 1
ccgactaacc atgcaaagtc gagcggatga cgggagcttg ctccttgatt cagcggcgga   60
cgggtgagta atgcctagga atctgcctgg tagtggggga caacgtttcg aaaggaacgc  120
taataccgca tacgtcctac gggagaaagc aggggacctt cgggccttgc gctatcagat  180
gagcctaggt cggattagct agttggtggg gtaatggctc accaaggcga cgatccgtaa  240
ctggtctgag aggatgatca gtcacactgg aactgagaca cggtccagac tcctacggga  300
ggcagcagtg gggaatattg gacaatgggc gaaagcctga tccagccatg ccgcgtgtgt  360
gaagaaggtc ttcggattgt aaagcacttt aagttgggag gaagggcagt aagttaatac  420
cttgctgttt tgacgttacc gacagaataa gcaccggcta actctgtgcc agcagccgcg  480
gtaatacaga gggtgcaagc gttaatcgga attactgggc gtaaagcgcg cgtaggtggt  540
ttgttaagtt ggatgtgaaa gccccgggct caacctggga actgcatcca aaactggcaa  600
gctagagtac ggtagagggt ggtggaattt cctgtgtagc ggtgaaatgc gtagatatag  660
gaaggaacac cagtggcgaa ggcgaccacc tggactgata ctgacactga ggtgcgaaag  720
cgtggggagc aaacaggatt agataccctg gtagtccacg ccgtaaacga tgtcaactag  780
ccgttggaat ccttgagatt ttagtggcgc agctaacgca ttaagttgac cgcctgggga  840
gtacggccgc aaggttaaaa ctcaaatgaa ttgacggggg cccgcacaag cggtggagca  900
tgtggtttaa ttcgaagcaa cgcgaagaac cttaccaggc cttgacatgc agagaacttt  960
ccagagatgg attggtgcct tcgggaactc tgacacagtg ctgcatggct gtcgtcagct 1020
cgtgtcttga gatgttgggt ttagtcccgt acgacgcaac cttgtcctta gtaccagcac 1080
gtatggtggg cactctagga aactgcgggt gacaaaccga aggaa           1125
```

PSEUDOMONAS MONTEILII STRAIN AND APPLICATION THEREOF IN THE DEGRADATION OF PETROLEUM HYDROCARBONS IN SALINE-ALKALI ENVIRONMENT

REFERENCE TO AN ELECTRONIC SEQUENCE LISTING

The contents of the electronic sequence listing (Name: SequenceListing.XXML; Size: 3,368 bytes; and Date of Creation: Aug. 1, 2023) is herein incorporated by reference in its entirety.

CROSS-REFERENCE TO RELATED APPLICATIONS

This application claims the benefit of priority from Chinese Patent Application No. 202210006424.3, filed on Jan. 5, 2022. The content of the aforementioned application, including any intervening amendments thereto, is incorporated herein by reference in its entirety.

TECHNICAL FIELD

This application relates to microbiology, and more particularly to a *Pseudomonas monteilii* strain and an application thereof in the degrading petroleum hydrocarbons in a saline-alkali environment.

BACKGROUND

As a major industrial lifeline of the contemporary economy, oil is widely used in major industrial fields. However, improper operation and leakage accidents in the process of oil exploitation, transportation, production and processing can cause environmental pollution. Petroleum hydrocarbons are one of the main components of oil, of which n-alkanes affect benthic organisms through long-term accumulation and geochemical action. In addition, polycyclic aromatic hydrocarbons are carcinogenic and threaten human life and health.

As a cost-effective, low-toxicity, and environmentally friendly strategy for oil pollution remediation, microbial remediation has attracted worldwide attention in recent years. However, the growth and remediation performance of microorganisms is often limited by pH and salinity. Generally, the optimal growth conditions for soil microorganisms are pH about 7.0 and salinity about 0.2%, and high salinity and excessive acidic or alkaline environments will inhibit the microbial activity. Some oil and gas development sites, such as Yumen Oilfield and Changqing Oilfield, are located in the northwest of China, where there is perennial drought and little water, salt and alkali are accumulated, and high pH and salinity of soil limit the microbial remediation of petroleum hydrocarbon pollution. In this experiment, the pH of the soils used at the sampling site of Changqing Oilfield was 7.12~8.58, and salinity was 1.4~2.1%. By 2017, the area of crude oil-contaminated soil in Longdong region, where Changqing oilfield is located, has reached $1.02 \times 10^4$ km$^2$, causing huge environmental pressure (Wang Jincheng, et al. Effects of petroleum hydrocarbon pollution on soil biology and non-biological characteristics of Longdong Loess Plateau[J]. Bulletin of Soil and Water Conservation, 2017, 37, (1): 9-16). Therefore, there is an urgent need for an affective method to solve the problem of oil contamination in the saline-alkaline soils.

SUMMARY

In view of the deficiencies in the prior art, this application provides a *Pseudomonas monteilii* strain with excellent salinity-alkalinity tolerance, which can be applied in the remediation of petroleum hydrocarbon pollution in a saline-alkali environment.

Technical solutions of this application are described as follows.

This application provides a *Pseudomonas monteilii* strain with salinity-alkalinity tolerance, wherein the *Pseudomonas monteilii* strain is *Pseudomonas* monteilii 9-2; the *Pseudomonas* monteilii 9-2 has been deposited in China General Microbiological Culture Collection Center (CGMCC, Institute of Microbiology Chinese Academy of Sciences, No. 1 Beichen West Road, Chaoyang District, Beijing, China) on Oct. 25, 2021, with an accession number of CGMCC No. 23666; and an internal transcribed spacer (ITS) sequence of the *Pseudomonas* monteilii 9-2 is shown in SEQ ID NO: 1.

The *Pseudomonas monteilii* CGMCC No. 23666 is isolated from the soil near the oil well platform of Changqing Oilfield in the Ordos Basin, and is domesticated with crude oil of the Changqing Oilfield as the only carbon source.

Biochemical and physicochemical characteristics of the *Pseudomonas monteilii* CGMCC No. 23666 are described as follows: rod-shaped; Gram-negative; negative for the starch hydrolysis test, lactose fermentation test, gelatin liquefaction test, indole test and methyl red test; positive for the contact enzyme assay; and the colonies are white with irregular edges.

The *Pseudomonas monteilii* CGMCC No. 23666 can degrade 83.99% of petroleum hydrocarbons after 14 days at 30° C., 150 r/min, pH 8.0, 3.0% salinity, and 1% (v: v) crude oil.

The *Pseudomonas monteilii* CGMCC No. 23666 has excellent salinity-alkalinity tolerance. Specifically, the tolerable pH range is 5.0~10.0, and the tolerable salinity range is 0.5%~6.0%.

This application has the following advantages and beneficial effects.

1. The *Pseudomonas monteilii* CGMCC No. 23666 has high stress resistance and tolerance, which can tolerate pH 5.0~10.0 and can tolerate the salinity up to 6%.
2. The *Pseudomonas monteilii* CGMCC No. 23666 can degrade 83.99% of petroleum hydrocarbons in a highly saline-alkali environment, exhibiting high petroleum hydrocarbon degradation efficiency, and good salinity-alkalinity resistance.

For those skilled in the art, without paying creative effort, other relevant drawings may be obtained according to these drawings.

DETAILED DESCRIPTION OF EMBODIMENTS

The technical solutions of the disclosure will be further described in detail in conjunction with embodiments.

Example 1 Isolation and Identification of *Pseudomonas* Monteilii 9-2

The petroleum hydrocarbons-containing surface soil at a depth of 5~10 cm around Changqing Oilfield was collected. 5 g of the surface soil was added to a sterilized Erlenmeyer flask containing 200 ml sterile water and incubated at 30° C., and 130 r/min under shaker shaking for 24 h. The Erlenmeyer flask after shock culture was left to stand for 1 h, and 5 mL of suspension was inoculated in 100 mL inorganic salt medium added to 1% crude oil of Changqing oilfield, and cultured in a shaker at 30° C. and 180 r/min for 10 days. After the culture, 5 mL of culture medium was aspirated and added to the same inorganic salt medium added to 1% crude oil of Changqing oilfield and incubated under the same conditions for 7 days, and so on, incubated 5 times continuously in a 7-day cycle. The bacterial solution was inoculated into Luria-Bertani (LB) solid medium with streak plate and cultured in a constant temperature incubator at 30° C. for 48 h. The purified strains on the plates were inoculated into beveled preservation medium and stored in a freezer at −18° C.

The purified strain was observed by Gram staining, biochemical and physicochemical characterization, morphology identification and scanning identification. The results showed: the strain was Gram-negative; test results of lactose fermentation test, indole test, starch hydrolysis test, gelatin liquefaction test, methyl red test (M.R), V.P. were negative; test results of contact enzyme and nitrate reduction assay were positive; the colonies were milky white with irregular edges; and single bacteria were rod-shaped.

The genomic DNA of the strain was acquired in the purified strain and amplified using the corresponding primers for polymerase chain reaction (PCR) amplification. The amplification products were sequenced by Guangdong Meige Gene Technology Co., Ltd. using ABI3730 sequencing platform. The sequencing results were compared on NCBI, and the phylogenetic tree was constructed by adjacency method according to the blast results. The results showed that the strain 9-2 involved in this disclosure was *Pseudomonas monteilii*, and internal transcribed spacer (ITS)sequence of the *Pseudomonas* monteilii 9-2 was shown in SEQ ID NO:1, and the similarity with the published strain (CP043396.1) was 100%. The *Pseudomonas monteilii* 9-2 has been deposited in China General Microbiological Culture Collection Center(CGMCC, Institute of Microbiology Chinese Academy of Sciences, No. 1 Beichen West Road, Chaoyang District, Beijing, China) on Oct. 25, 2021, with an accession number CGMCC No. 23666.

Example 2 Test of Stress Resistance of *Pseudomonas* Monteilii 9-2

Figure 1:
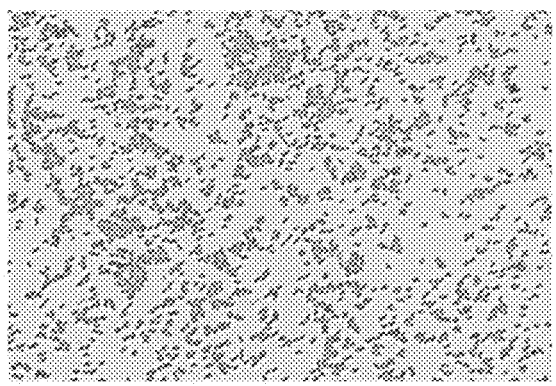
FIG. 1 is an image showing colony morphology of *Pseudomonas monteilii* according to an embodiment of the present disclosure.
Figure 2:
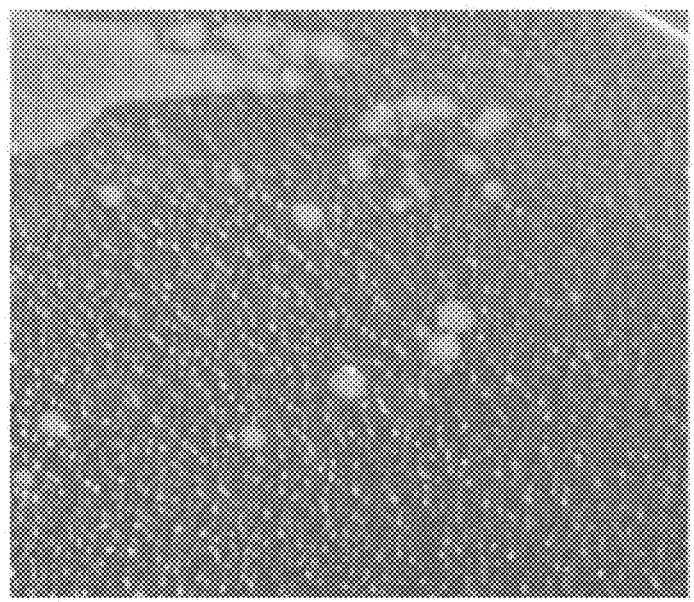
FIG. 2 is a micrograph of *Pseudomonas monteilii* after Gram staining.
Figure 3:
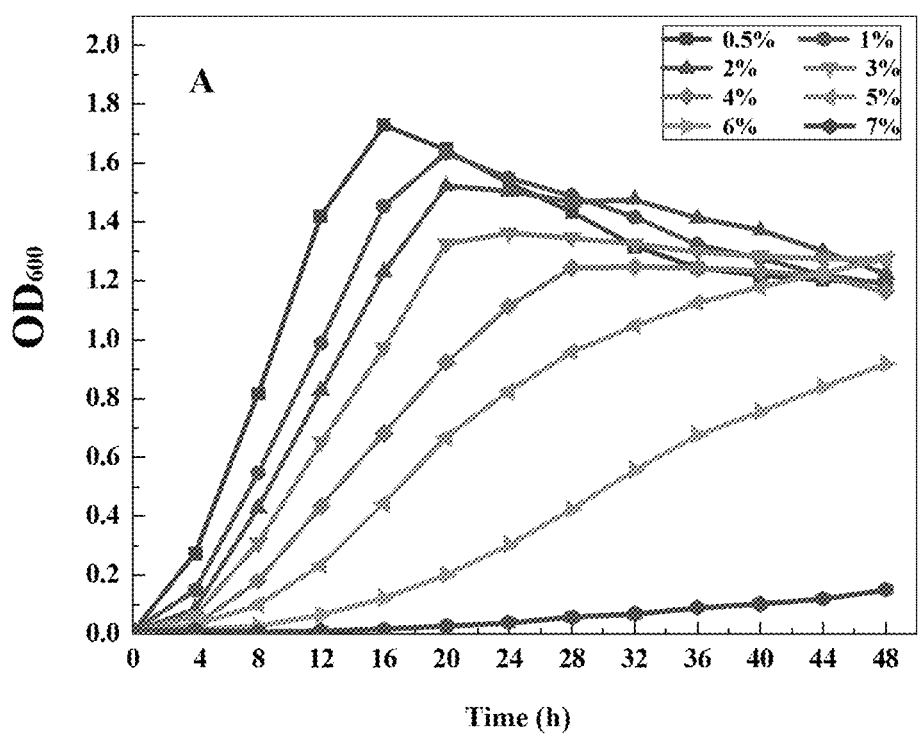
FIG. 3 is a growth curve of *Pseudomonas monteilii* cultured for 48 h at different salinities.

100 mL of enrichment medium was adjusted to salinity 0.5%, 1.0%, 2.0%, 3.0%, 4.0%, 5.0%, 6.0%, 7.0% and 8.0% with NaCl, and three parallel groups were set for each salinity gradient. After inoculating the strain into 100 mL of enrichment medium for 48 h, a pure bacterial solution with a concentration of OD 600=0.5 was prepared with sterilized PBS solution, inoculated into the medium with 5% inoculation amount, and incubated at 30° C., and 150 r/min for 48 h. The absorbance at a wavelength of 600 nm was measured with a UV/VIS spectrophotometer with sterilized enrichment medium as a control group every 4 h. The results were shown in FIG. 3. *Pseudomonas* monteilii 9-2 grew fastest in the log growth phase at 0.5% salinity, was suitable for growth at 0.5%~5.0% salinity, and relatively weakened at 6.0% salinity. Therefore, *Pseudomonas* monteilii 9-2 can tolerate salinity below 6.0% and stunted at 7.0% salinity Similarly, NaOH and HCl were used to adjust the pH of the enrichment medium to 3.0, 4.0, 5.0, 6.0, 7.0, 9.0, 10.0 and 11.0, respectively, and three parallel groups were set up for each pH level. After inoculating the strains into 100 mL of enrichment medium for 48 h, a pure bacterial solution with a bacterial concentration of OD 600=0.5 was prepared with sterilized PBS solution, inoculated with 5% inoculation into medium with different pH values, and incubated at 30° C. and 150 r/min for 48 h. Sterilized enrichment medium was used as a blank group. The absorbance at wavelength 600 nm was measured with a UV/VIS spectrophotometer every 4 h.

Figure 4:
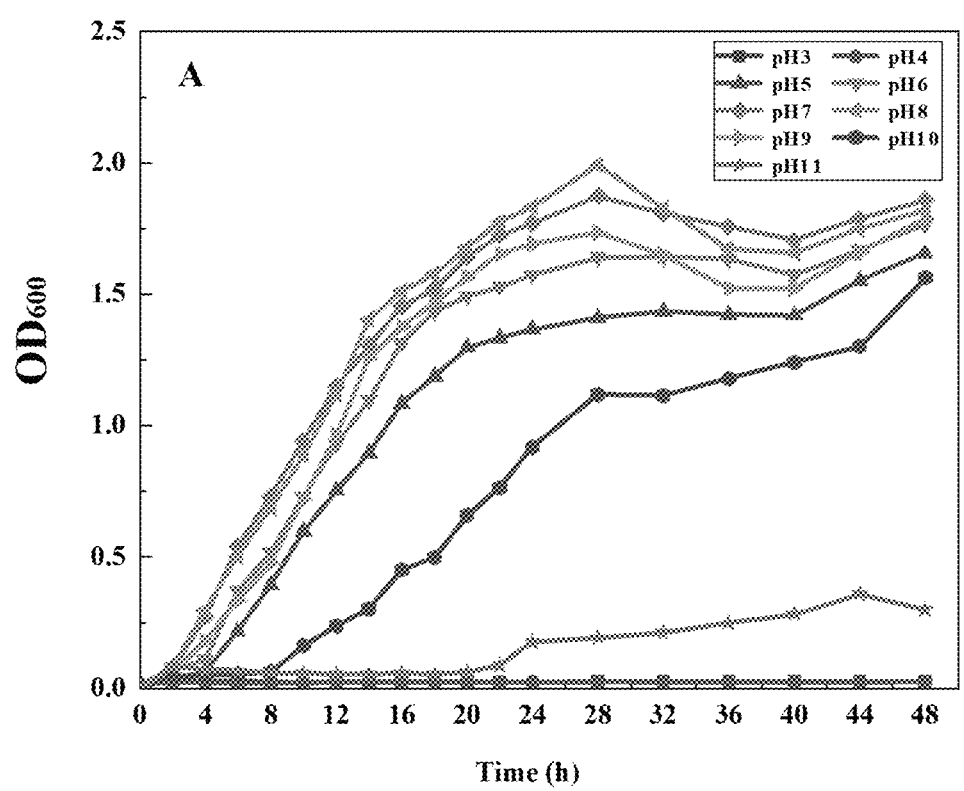
FIG. 4 is a growth curve of *Pseudomonas monteilii* cultured for 48 h at different pH values.

The results were shown in FIG. 4, *Pseudomonas* monteilii 9-2 grew well in the pH range of 5.0~10.0 and grew slow at pH 11 and almost stopped growing at pH 3.0 and pH 4.0.

The medium formulation involved in the embodiment was as follows.

Trace element solution: $FeSO_4$ 0.054 g, $MnSO_4$ 2.3 g, $CuSO_4$ 0.032 g, ultrapure water 1000 mL.

Inorganic salt medium: $KH_2PO_4$ 2.42 g, $K_2HPO_4$ 7.3 g, $(NH_4)_2SO_4$ 2 g, NaCl 2 g, $MgSO_4$ 0.3 g, $CaCl_2$) 0.03 g, trace element solution 1 mL, ultrapure water 1000 mL. pH was adjusted to 7.0 with NaOH and hydrochloric acid. Sterilization operation was performed in an autoclave for 20 min.

Enrichment medium (beef paste peptone medium): beef extract 5 g, peptone 10 g, NaCl 5 g, ultrapure water 1000 mL, adjusted to pH 7.4 with NaOH and hydrochloric acid, sterilized in autoclave for 20 min.

Beveled preservation medium: beef paste 5 g, peptone 10 g, NaCl 5 g, agar powder 15 g, ultrapure water 1000 mL, adjusted to pH 7.4 with NaOH and hydrochloric acid, sterilized in an autoclave for 15 min.

Example 3 Degradation of Crude Oil in a Saline-Alkaline Environment in the Presence of *Pseudomonas* Monteilii 9-2

After incubating the fresh strain in 100 mL enrichment medium for 48 h, a pure bacterial solution with a bacterial concentration of OD 600=0.5 was prepared in sterilized PBS solution, inoculated with 5% inoculation into an inorganic salt medium with 1% crude oil as the only carbon source, and adjusted to pH 8.0 and 3.0% salinity in a high saline-alkaline environment. Three parallel samples were set up in per group and incubated at 30° C., 180 r/min for 14 days. The samples were then extracted with 20 mL of petroleum ether with a boiling range of 60~90° C., and each sample was extracted three times and the extracts were combined. Crude oil extracted from crude oil medium without bacterial agents was used as the control group. The supernatant was extracted by centrifugation three times, absorbed water with $Na_2SO_4$ and transferred to a volumetric flask, and then made up to 20 mL with petroleum ether. After full shaking, 200 μL of sample was removed with a pipette and added 100 μL of 0.3 mg/mL $C_{24}D_{50}$ and 500 μL of 0.05 mg/mL deuterated naphthalene as internal standard. The samples were analyzed by gas chromatography-mass spectrometry (GC-MS) using an Agilent 6890N (GC)/5973B (MSD) gas chromatograph mass spectrometer. The degradation rate of each component of petroleum hydrocarbons was calculated by integrating the peak area of the gas chromatogram.

Figure 5A:
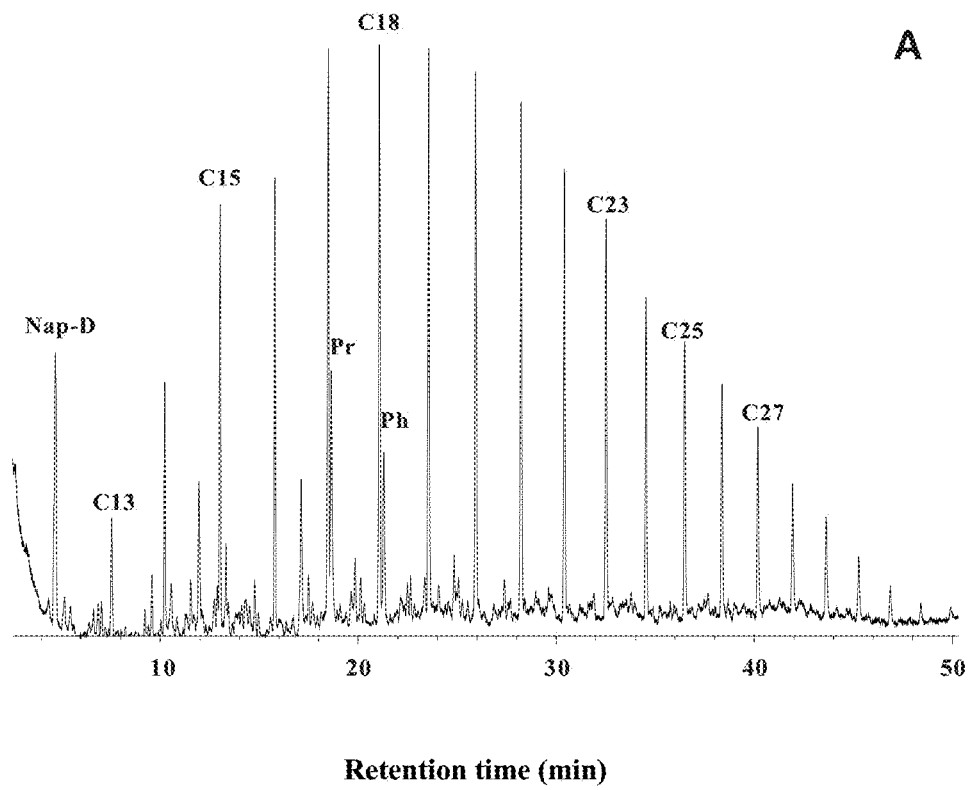
FIGS. 5A and 5B show gas chromatograms of crude oil before and after degradation, where (5A) before inoculation with *Pseudomonas monteilii*; and (5B) 14 days after inoculation with *Pseudomonas monteilii* (Nap-D is the internal standard deuterated naphthalene; Pr is pristane; and Ph is phytane)
Figure 5B:
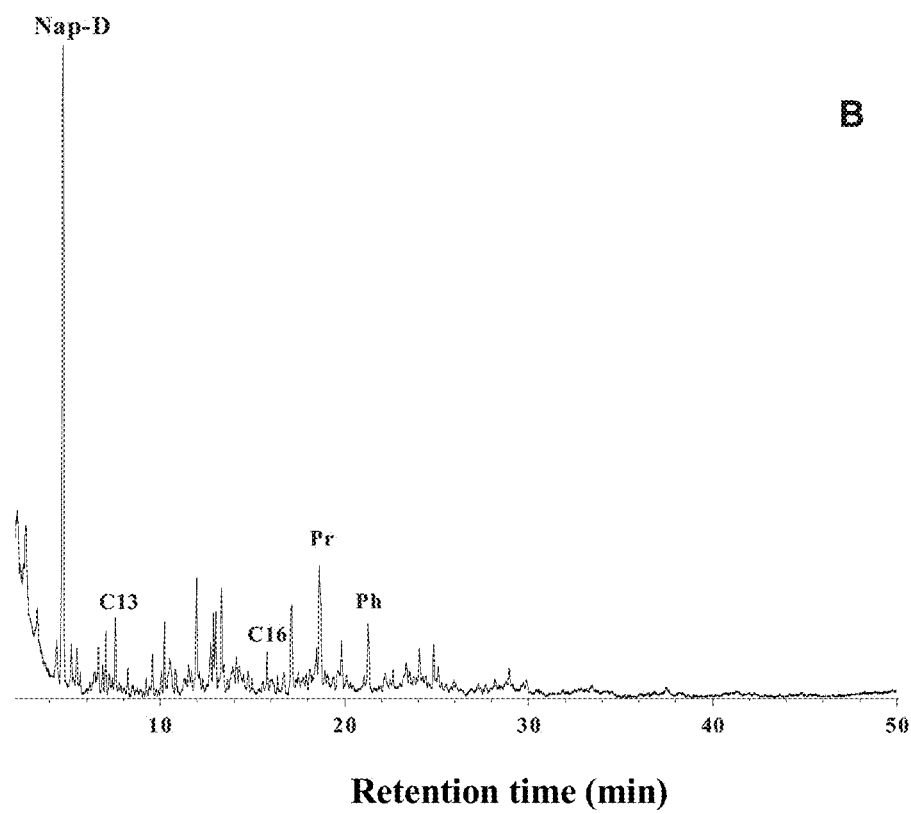
Figure 6:
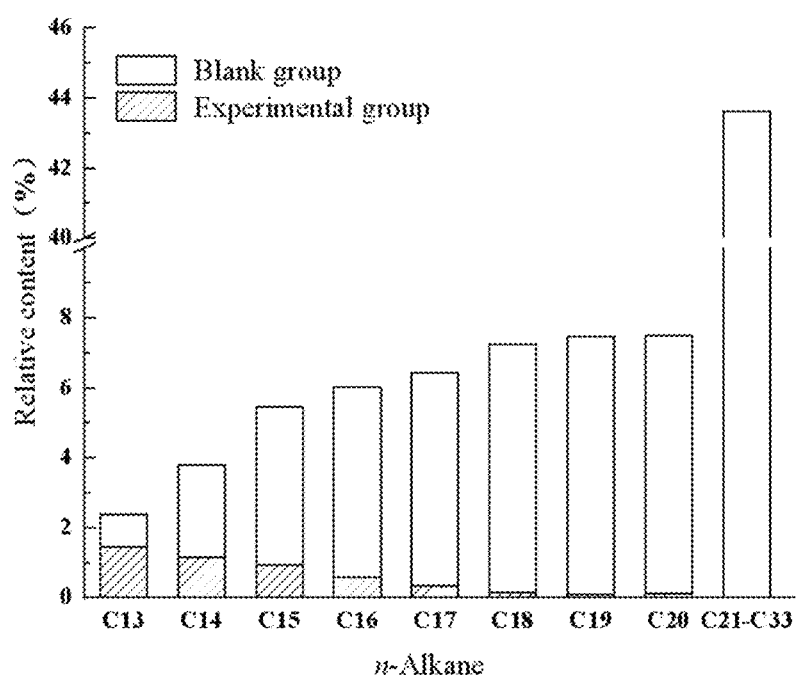
FIG. 6 shows relative content of n-alkanes varying in carbon number in saturated hydrocarbons before and after degradation.

The results were shown in FIGS. 5A and 5B, and *Pseudomonas* monteilii 9-2 has degraded 83.99% of petroleum hydrocarbons after 14 days at 1% (v: v) crude oil. As showed in Table 1, after 14 days shaker culture, n-alkanes ($nC_{13}$ to $nC_{20}$) were degraded by 38.85%, 69.88%, 82.84%, 90.38%, 94.69%, 98.13%, 98.58% and 98.45%, respectively. The levels of $n-C_{21}$ to $n-C_{33}$ in the degraded residual oil were all less than the limit of detection (LOD) which showed that *Pseudomonas* monteilii 9-2 had good degradation effect on both short-chain and long-chain n-alkanes and had better degradation effect on long-chain n-alkanes. The relative content of n-alkanes with different carbon numbers in saturated hydrocarbons before and after degradation by *Pseudomonas* monteilii 9-2 was shown in FIG. 6.

TABLE 1 n-Alkane levels before and after degradation

| n-Alkanes | Relative abundance before degradation | Relative abundance after degradation | Degradation rate |
|---|---|---|---|
| n-Tridecane | 0.071404133 | 0.043664025 | 38.85% |
| n-Tetradecane | 0.113595713 | 0.034217726 | 69.88% |
| n-Pentadecane | 0.163116819 | 0.027992254 | 82.84% |
| n-Hexadecane | 0.180077909 | 0.017318016 | 90.38% |
| n-Heptadecane | 0.19226222 | 0.010206825 | 94.69% |
| n-Octadecane | 0.217283445 | 0.004072959 | 98.13% |
| n-Nonadecane | 0.22355184 | 0.0031823 | 98.58% |
| n-Eicosane | 0.224348619 | 0.003474945 | 98.45% |
| n-Heneicosane | 0.224650571 | less than LOD | 100.00% |
| n-Docosane | 0.201068518 | less than LOD | 100.00% |
| n-Tricosane | 0.186100179 | less than LOD | 100.00% |
| n-Tetracosane | 0.157336585 | less than LOD | 100.00% |
| n-Pentacosane | 0.143195257 | less than LOD | 100.00% |
| n-Hexacosane | 0.114506027 | less than LOD | 100.00% |
| n-Heptacosane | 0.099547971 | less than LOD | 100.00% |
| n-Octacosane | 0.065699944 | less than LOD | 100.00% |
| n-Nonacosane | 0.054168941 | less than LOD | 100.00% |
| n-Triacontane | 0.034343377 | less than LOD | 100.00% |
| n-Hentriacontane | 0.014539767 | less than LOD | 100.00% |
| n-Dotriacontane | 0.008990165 | less than LOD | 100.00% |
| n-Tritriacontane | 0.002953559 | less than LOD | 100.00% |

These embodiments are only illustrative of the present disclosure, and are not intended to limit the present disclosure. It should be understood that any variations, modifications and replacements made by those skilled in the art based on the content disclosed herein without paying creative effort should fall within the scope of the disclosure defined by the appended claims.

What is claimed is:

1. A method for degrading petroleum hydrocarbons in a saline-alkali environment, comprising:
    contacting a *Pseudomonas monteilii* strain with crude oil to degrade the petroleum hydrocarbons in the crude oil;
    wherein the *Pseudomonas monteilii* strain is *Pseudomonas* monteilii 9-2, which has been deposited in China General Microbiological Culture Collection Center (CGMCC) on Oct. 25, 2021 with an accession number of CGMCC No. 23666; and an internal transcribed spacer (ITS) sequence of the *Pseudomonas* monteilii 9-2 is shown in SEQ ID NO: 1.

2. The method of claim 1, further comprising: preparing a bacterial solution of the *Pseudomonas monteilii* strain.

3. The method of claim 2, wherein contacting the *Pseudomonas monteilii* strain with the crude oil comprises: inoculating the bacterial solution of the *Pseudomonas monteilii* strain into a culture medium comprising the crude oil.

4. The method of claim 3, wherein the crude oil is a sole carbon source in the culture medium.

5. The method of claim 4, wherein the culture medium has a pH of 8.0 and a salinity of 3.0%.

6. The method of claim 1, wherein the *Pseudomonas monteilii* strain is capable of being tolerant to a pH of 5.0~10.0 and a salinity of 0.5%~6.0%.

\* \* \* \* \*